United States Patent [19]

Beisang, III et al.

[11] Patent Number: 5,395,344
[45] Date of Patent: Mar. 7, 1995

[54] CATHETER ANCHORING DEVICE

[75] Inventors: Arthur A. Beisang, III; Arthur A. Beisang, both of Shoreview, Minn.

[73] Assignee: Genetic Laboratories Wound Care, Inc., St. Paul, Minn.

[21] Appl. No.: 10,971

[22] Filed: Jan. 29, 1993

Related U.S. Application Data

[63] Continuation-in-part of Ser. No. 824,735, Jan. 21, 1992, abandoned, which is a continuation of Ser. No. 535,331, Jun. 8, 1990, abandoned.

[51] Int. Cl.$^6$ .............................................. A61M 5/32
[52] U.S. Cl. .................................. 604/180; 604/174; 128/DIG. 26
[58] Field of Search ............... 128/DIG. 6, DIG. 26, 128/912; 604/174, 177, 179, 180, 307, 344, 351; 602/54, 57; 24/DIG. 11, 483, 484

[56] References Cited

U.S. PATENT DOCUMENTS

| | | |
|---|---|---|
| 1,052,274 | 2/1913 | Purdy . |
| 3,138,158 | 6/1964 | Gordon et al. ............ 128/DIG. 26 |
| 3,146,778 | 9/1964 | Krawiec ...................... 24/DIG. 11 |
| 3,286,713 | 11/1966 | Kurtz et al. .......................... 604/305 |
| 3,368,564 | 2/1968 | Selix .............................. 128/DIG. 26 |
| 3,430,300 | 3/1969 | Doan . |
| 3,677,250 | 7/1972 | Thomas . |
| 3,683,911 | 8/1972 | McCormick . |
| 3,782,377 | 1/1974 | Rychlik . |
| 3,856,020 | 12/1974 | Kovac . |
| 3,900,026 | 8/1975 | Wagner . |
| 3,983,297 | 9/1976 | Ono et al. . |
| 4,024,312 | 5/1977 | Korpman . |
| 4,059,105 | 11/1977 | Cutruzzula et al. . |
| 4,074,397 | 2/1978 | Rosin ............................ 128/DIG. 26 |
| 4,165,748 | 8/1979 | Johnson . |
| 4,235,234 | 11/1980 | Whitney et al. . |
| 4,302,500 | 11/1981 | Flora . |
| 4,324,236 | 4/1982 | Gordon et al. . |
| 4,324,237 | 4/1982 | Butteravoli .......................... 602/54 |
| 4,333,468 | 6/1982 | Geist . |
| 4,346,700 | 8/1982 | Dunshee et al. . |
| 4,380,234 | 4/1983 | Kamen . |
| 4,457,754 | 7/1984 | Buttaravoli ................. 128/DIG. 26 |
| 4,460,356 | 7/1984 | Moseley . |
| 4,484,914 | 11/1984 | Brown .................................. 604/180 |
| 4,490,141 | 12/1984 | Lacko et al. . |
| 4,534,762 | 8/1985 | Heyer . |
| 4,548,200 | 10/1985 | Wapner ...................... 128/DIG. 26 |
| 4,569,348 | 2/1986 | Hasslinger ........................... 604/179 |
| 4,627,842 | 12/1986 | Katz . |
| 4,704,177 | 11/1987 | Vaillancourt . |
| 4,726,716 | 2/1988 | McGuire . |
| 4,737,143 | 4/1988 | Russell . |
| 4,743,232 | 5/1988 | Kruger ............................... 604/307 |
| 4,822,342 | 4/1989 | Brawner . |
| 4,838,868 | 6/1989 | Forgar et al. . |
| 4,863,432 | 9/1989 | Kvalo . |
| 4,941,882 | 7/1990 | Ward et al. . |
| 5,098,399 | 3/1992 | Tollini . |
| 5,221,265 | 6/1993 | List ..................................... 604/180 |

FOREIGN PATENT DOCUMENTS

| | | |
|---|---|---|
| 0416655 | 9/1934 | United Kingdom . |
| 2211417 | 7/1989 | United Kingdom . |

Primary Examiner—C. Fred Rosenbaum
Assistant Examiner—Ronald K. Stright, Jr.
Attorney, Agent, or Firm—Haugen and Nikolai

[57] ABSTRACT

A one or two-piece, one-time or reusable catheter anchoring system is disclosed which may be utilized to facilitate the anchoring of a urinary catheter, an umbilical catheter or other draining device to the thigh or abdomen of the patient in a manner which prevents irritation and accidental dislodgement.

8 Claims, 4 Drawing Sheets

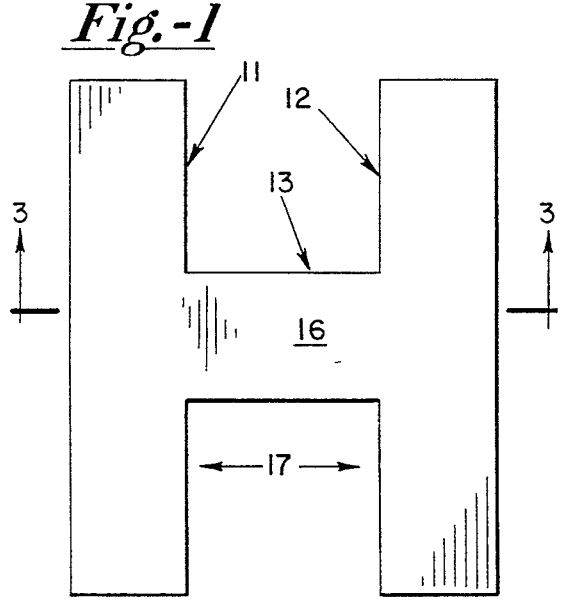
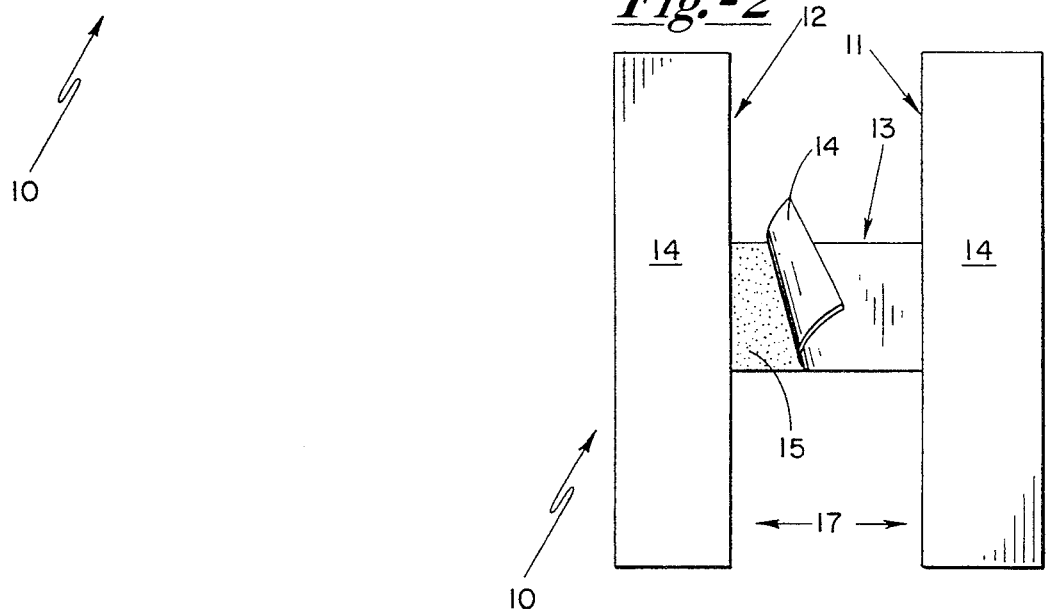
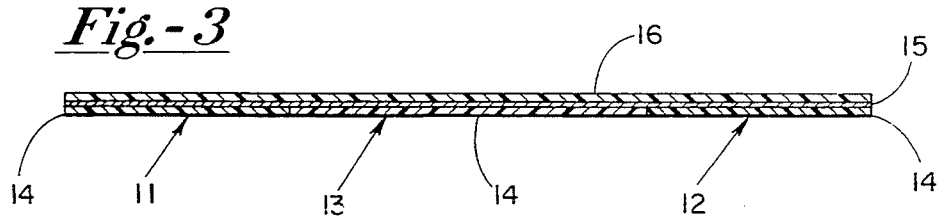

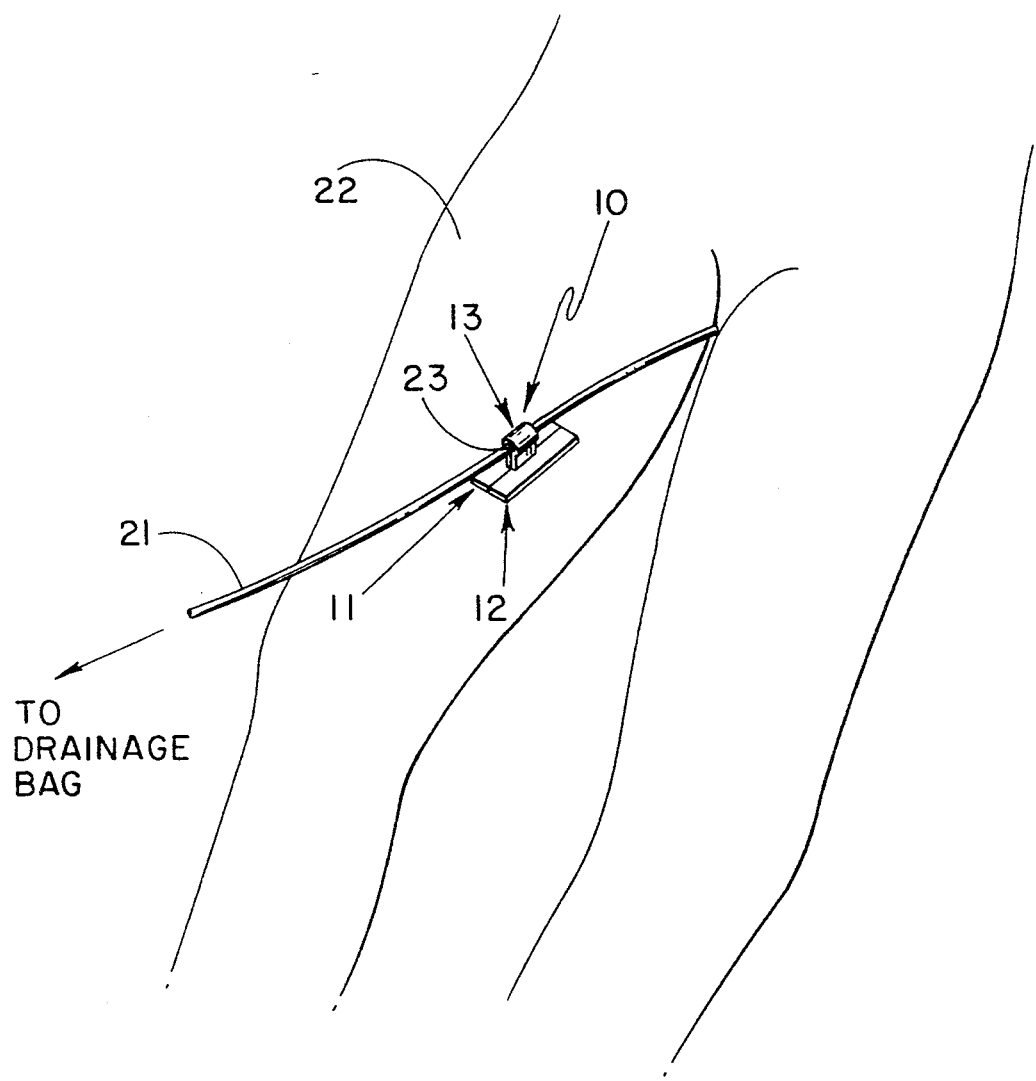

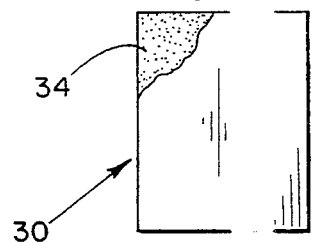
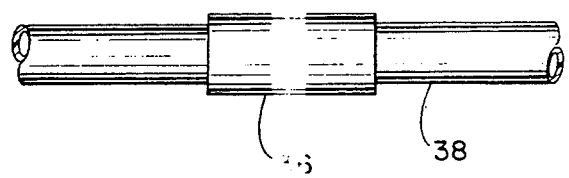
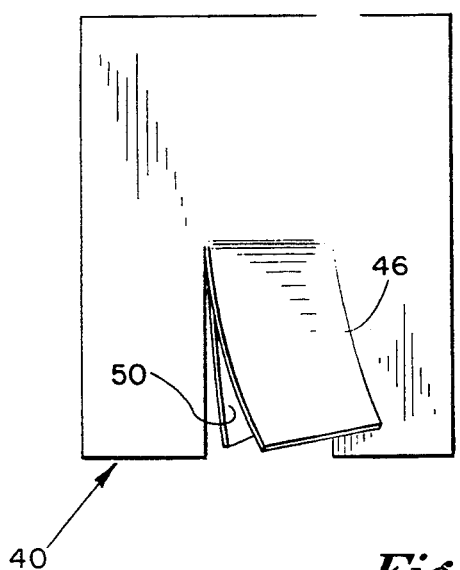
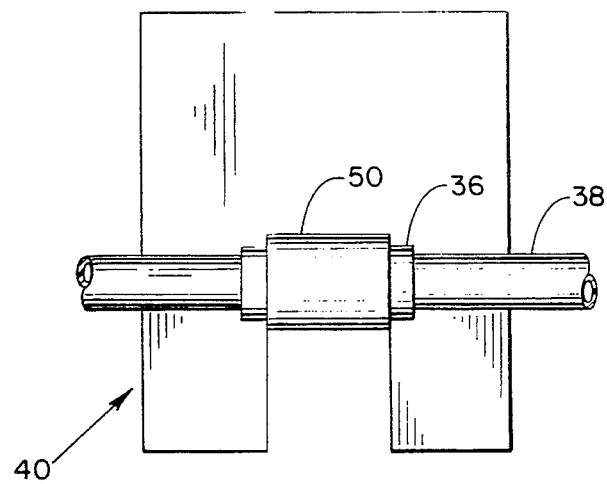
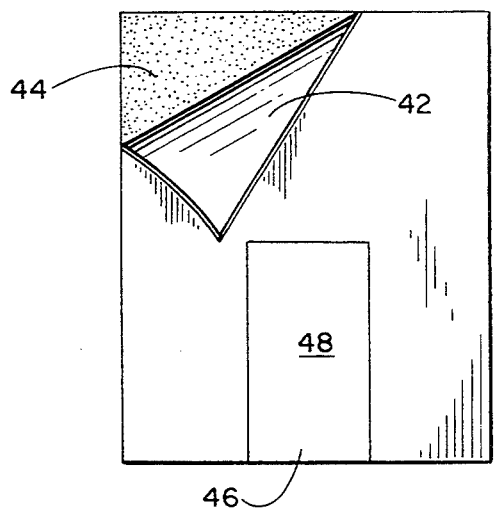

CATHETER ANCHORING DEVICE

CROSS-REFERENCE TO RELATED APPLICATION

This patent application is a continuation-in-part of application Ser. No. 07/824,735, filed Jan. 21, 1992, now abandoned, which, in turn, is a continuing application of Ser. No. 07/535,311, filed Jun. 8, 1990, now abandoned.

BACKGROUND OF THE INVENTION

1. Field of the Invention

The present invention relates generally to the field of disposable devices for anchoring bodily mounted drainage tubes such as urinary catheters and the like and, more particularly to a prefabricated device especially configured to facilitate its attachment to the drainage tube, or the like, and to the skin of a patient.

2. Discussion of the Related Art

During the course of certain medical procedures, and particularly, after surgery, it is necessary to place drainage devices to prevent accumulation of fluids in various bodily cavities or organs. One of the most common of these, of course, is the urinary catheter which is generally routed through the patient's urethral opening or superpubic ostomy site. It is important to anchor the catheter device so that there is little movement with respect to the insertion site to minimize irritation. In the case of the urinary catheter the tube normally has a very long length and is hooked to a rather large bag, so it is quite easy to catch the catheter and bag which may result in dislodgement of the catheter, which, in turn, causes great pain to the patient and possibly actual physical damage.

One common practice associated with immobilizing such things as catheter tubes has been to simply use several sections of adhesive tape to secure the tubing to the patient's body at a convenient spot between the insertion site and the collection bag. An alternative practice with respect to the urinary catheter has been to use a cloth retainer which fastens around the leg and has some form of cloth or plastic catheter holding device attached to it.

Both of these approaches, of course, have drawbacks. In the case of the tape, it is cumbersome to use and remove and also, because it is rigid, it does not move with the compliance modulus of the skin. The cloth wrapped around the leg has a tendency to slide downward as the leg naturally narrows from the proximal to the distal approaching the knee. This requires multiple adjustments to keep the leg band in position. In addition, the system does not provide for fixing the catheter tube in place and it tends to slip through the cloth loop and can possibly detach completely with a light pull. This is especially true in view of the fact that to reduce friction between the tube and the tissue it engages at the insertion site, the tube is normally made of reduced friction material such as a silicone plastic or the like or possibly, in the alternative, is coated with a hydrophilic material which causes the material to exhibit a non-stick surface. These developments represent progress with respect to the insertion of the catheter tube into the body in terms of ease and comfort to the patient. However, they also cause difficulties with respect to anchoring the tube because of the increased likelihood of slipping of the catheter tube with respect to the tape or cloth anchor device. The need still exists for a more positive support which retains the quality of being gentle to the patient.

Additional devices have also been proposed. A one-piece catheter anchoring tube or holder is disclosed by Johnson in U.S. Pat. No. 4,165,748, in which a piece of material has adhesive on one surface and is in the shape of a narrow bridge of the material that connects two larger spaced rectangular skin addressing segments. The device has two larger segments designed to adhere to the skin of the patient and the narrow or bridge portion uses the adhesive on the skin side directed to adhere to itself, forming a double fold layer. The double layer, in turn, wraps around the tube to be secured and is further provided with fasteners such as snap fasteners or Velcro ® for securing the double thickness loop to itself after encircling the tube. The tube can be released and resecured but must rely on the friction of the tube encircling loop alone to anchor the tube longitudinally once fixed in position. Thus, the tube can be easily dislodged in the directional parallel to its length and slidably displaced while secured in the loop.

A further device is shown in U.S. Pat. No. 3,677,250 to Thomas that discloses embodiments in which anchoring or skin adhering sections or patches are provided with integral tabs which are designed to wrap about the tubes to be secured, fixing them tangentially or parallel to the skin against the upper side of the skin anchoring patch. The tabs may permanently adhere to the surface of the tube in a non-reusable manner or, as in one embodiment, a pair of opposing tabs are provided which removably adhere to each other and slidably retain the tube or tubes therebeneath. This one-piece arrangement either does not allow for removal, replacement or adjustment of the tube or, in the case of the removable, readherable embodiment, suffers from the same ease of slidable tube displacement associated with other prior devices.

SUMMARY OF THE INVENTION

In accordance with the present invention, there is provided a prefabricated adhesive or strip patch which is preshaped to facilitate its attachment to a drainage device such as a urinary catheter tube, or the like, and to the surface of the patient's thigh or abdomen as the case may be. The device is substantially easier to use and apply and enables a more positive retention of the tube in place. The catheter tube anchoring device may be in the form of a one or two-piece system and may use a reusable or readherable adhesive to fasten the tube to be secured. The tube may be secured in a vertical or horizontal position with respect to the body surface or at any angle therebetween, i.e., at 0–90° with respect to any attached body surface.

One preferred construction of the anchoring device of the present invention includes the use of a thin plastic backing sheet material for adherence to the skin of the type which exhibit asymmetrical or uniaxial stretch properties, permeability to moisture and air, and a compliance modulus closely resembling that of human skin. For human skin a compliance modulus, irrespective of thickness, in the range of from about 0.5 to about 110 pounds per inch along with an elastic recovery somewhat less than 99% is typical.

One embodiment of the tube anchoring device of the present invention is of a precut shape which preferably has a rectangular tube engaging zone attached on both sides to flanking rectangular skin engaging zones. This results in a configuration for most applications closely resembling a block "H" shape in which the horizontal member of the "H" is the tube engaging zone. The easier stretchable axis direction of the asymmetrically stretchably material is preferably aligned parallel to the shorter dimensions of the skin engaging zones and perpendicular to the shorter dimensions of the tube engaging zones or horizontally with respect to the H-shape previously described. One side of the material is covered with a self-adhering, bio-compatible, non-allergenic adhesive such as, for example, polymethacrylate, polyvinyl ethyl ether, polyacrylate or acrylic ester copolymer. The adhesive material is strong enough to rigidly mount the tube and hold the mounting to the skin yet is removable without damaging the skin. Prior to application, the adhesive layer is covered with a peel away backing or release paper layer which maintains the integrity of the system until use.

In application, the urinary catheter or other drainage tubular device is first inserted in the superpubic or another ostomy site, in the position desired with the tube extending therefrom to a collection device such as a bag. The tube is then ready to be anchored using the device of the invention. The portions of the release paper covering the middle or catheter tube engaging zone are peeled away and removed, the catheter tube is aligned with the middle of the catheter tube engaging zone and the catheter tube engaging zone is then wrapped around the full 360 degree of the tube and the rest of the engaging zone is then adhered to itself beyond the tube to form a webbing. The release papers are then peeled away from the two skin engaging zones and they are attached adhesively to the skin juxtaposed beneath the tube at a spot that allows for comfortable positioning of the tube.

The tube engaging zone of the tube anchoring system of the invention is preferably made longer than is necessary for the 360 degree peripheral engagement of the tube being anchored so that when the two skin engaging portions are anchored the amount of webbing formed by the additional self-adhering portion of the tube engaging section may be varied to allow the tube to be spaced at the desired distance from the skin.

Because the above-described physical properties of the backing material include an asymmetric elasticity together with certain recovery properties, the device when applied to the skin exhibits properties similar to that of the skin to which it is applied and can mimic the movement of the skin sufficiently to inhibit it from wrinkling and coming loose from the skin's surface. The urinary catheter tube anchor is designed to allow an amount of flexibility or changes in catheter position. The webbing that is formed by folding the tube engaging zone is somewhat flexible, and additionally, the self-adhering double thickness of material between the tube and the skin enhances the strength of the device at the point where forces opposing adherence are greatest.

Several alternative two-piece anchoring arrangements are also provided in which a smaller tab portion fastens peripherally about the tube to be anchored and cooperates with a larger patch portion that is adhered to the skin. The tube tab and skin patch cooperate to anchor the tube in place optionally in a removable, replaceable or one-use fashion. With these embodiments, preferably the tube tab permanently adheres to the tube and the skin patch remains attached to the skin while the tube tab attached to the tube cooperates with the skin patch to removably and replaceably attach and anchor the tube. In this manner, in the two-piece arrangement, the tube to be attached is provided with a tab or tube patch which has an adhesive side which will securely attach the patch to the catheter. The other surface allows for multiple cycles of attachment and detachment from the anchoring or skin patch portion of the two-piece anchoring arrangement. Three examples of the arrangement which allow for repeated detachment and reattachment are:

(1) an outer surface of the tube patch which has a surface allowing the adhesive of the skin patch to reversibly attach to it;

(2) a similar arrangement of the tube patch with adhesive on the outer portion and attachment to a suitable material on the skin patch;

(3) an arrangement of hooks and loops.

The tube tab may use a permanent adhesive which readily bonds even to silicon tubing in addition to polyolefin materials such as polyethylene and other tubing materials.

The mating surfaces of the skin anchoring or skin patch portion and the tube tab of the two-piece anchoring arrangement combine with sufficient retentive force to hold the tube in place, as needed, but in a manner which allows easy removal and readhesion to permit temporary removal or adjustment of tube placement. Of course, additional tube tabs may be spaced along the tube and utilized to move the tube with respect to the skin patch or skin anchor, as desired. In addition, the tube tab may optionally also be secured to the tube itself using a removable readhesible adhesive material having the required attachment/removal force.

Using the present invention, a urinary catheter tube or other type ostomy tube can be anchored in a matter of moments and in a manner which provides a neat-appearing, positive placement and dependable retention system for the tube to assure hours, or even days, if necessary, of comfortable use by a patient.

BRIEF DESCRIPTION OF THE DRAWINGS

In the drawings:

FIG. 1 is a top view of the tube anchoring device representing the system as it might appear upon its removal from an aseptic package prior to application;

FIG. 2 is a bottom view, partially in perspective, of the tube anchoring device of FIG. 1 with the release paper partially peeled back to reveal the adhesive layer;

FIG. 3 is a crossectional view of the layered structure of the tube anchoring device of the invention;

FIG. 4 is an anterior perspective view showing a typical manner in which the tube anchoring device of the present invention is applied to a patient;

FIG. 5A is a tube tab for use with alternate two-piece embodiments of the anchoring device of the invention;

FIG. 5B shows the tube tab of FIG. 5A secured about a tube;

FIGS. 6A-6B illustrate the anchoring segment of one two-piece arrangement;

FIG. 6C illustrates the manner in which the two-piece anchoring device is assembled in use with the permanently secured tube tab of FIG. 5B.

DETAILED DESCRIPTION

Figure 7A:
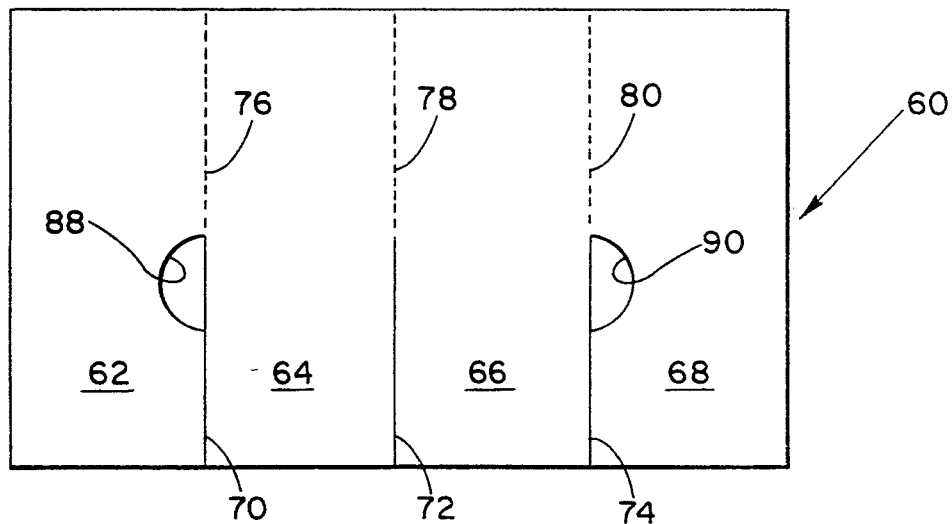
FIGS. 7A-7C illustrate another two-piece embodiment of the present invention.

The catheter anchoring arrangement of the present invention is one in which the catheter tube, once fixed in position in accordance with the anchoring system of the invention cannot slide or otherwise be readily displaced or dislodged, as by inadvertent movement of the patient or other means, as it is adhesively retained rather than being retained against longitudinal sliding by frictional means. The tube of interest may be retained in a disposition substantially parallel to or even perpendicular to the skin area to which it is anchored, depending on the embodiment selected. Even with regard to embodiments in which the catheter tube may be removed and replaced with respect to the skin adhering portion, or the tube tab removed and replaced on the tube, once secured in place in a given location, the tube cannot be moved without dislodging the fastening means.

As depicted in FIGS. 1 and 2, the tube anchoring device of the present invention is seen generally at 10 and approximate the shape of an "H" in which two segments 11 and 12 are designed to anchor the third or tube engaging segment 13 to the patient's skin. The underside is illustrated in FIG. 2 with part of the backing material 14 removed from the section 13 to show an adhesive layer 15. The adhesive layer 15, of course, is common to the entire surface of the device although, if desired, diverse adhesives may be used for the tube engaging section 13 and the skin engaging sections 11 and 12 if the material of the tube requires such. The material of construction comprising the plastic underlayer of the device 16 (FIG. 3), as described above, is preferably formed from either a woven or non-woven polymeric material having a pattern of fibers or the like orientated therein so as to exhibit a preferred or easy direction of stretch identified by the arrow 17 in FIGS. 1 and 2.

The basic plastic or polymer material of the device must also be of a type that is pervious to moisture and air so that it allows the area beneath where it is applied to the skin to "breathe". As previously stated the preferred asymmetric nature of the easy axis of elasticity of the material normally dictates the cutting angle when large numbers of the devices are produced from sheets of material such that the easy stretch axis 17 is at the desired predetermined posture such that the devices produced exhibit the desired compliance modulus and elastic recovery. As previously stated, it has been found that a compliance modulus irrespective of thickness in the range of from 0.5 to 110 pounds per inch and an elastic recovery factor less than 99% yields excellent results in that the resulting product is found to exhibit stretch characteristics correspondingly close to that of skin. This means that the anchoring device will flex with the skin movement in a coordinated manner thereby avoiding puckering and detachment of the anchor.

The layered structure of the anchoring device is shown in FIG. 3 and includes the release paper layer 14, the adhesive layer 15 and the layer of plastic or polymeric material 16. The layer of backing or release paper 14 protects the integrity of the adhesive layer 15 prior to use. The release paper is sectioned such that continuous pieces cover the three segments of the anchoring devices 11, 12 and 13.

FIG. 4 depicts the anchoring system of the invention as used to anchor a urinary catheter 21 which has been routed through the patient's urethra and into the bladder at one end and proceeds to an ostomy bag (not shown) at the distal end. As noted in the illustration of FIG. 3, the central or tube engaging portion 13 wraps around the catheter tube 21 and contains sufficient additional material such that it spaces the tube 21 from the patient's leg 22 illustrated at 23. The skin attachment zones in 11 and 12 are shown in abutting juxtaposed parallel arrangement beneath the tube and secured to the skin by the adhesive material. The tube engaging portion 13 engages the entire 360 degree periphery of the tube and thereafter self-adheres. In addition to spacing the tube 21 from the leg 22 the extra material of the tube engaging segment 13 provides a double thickness tab for securing the tube 21 which is strong and yet flexible to accommodate movement and thereby decrease the stress that is placed on the skin attachment zones 11 and 12.

Additional problems are encountered in nursing homes, hospitals and other patient care facilities in situations in which it is necessary to fasten tubes such as catheter tubes firmly but in a manner in which a tube can be removed and replaced in its firmly secure position. In other situations, the tube of interest may have to be secured at different angles with respect to the skin and even perpendicular to the skin as in the case of umbilical cord catheters or some other catheters entering surgical body openings. Accordingly, the invention contemplates and provides alternate embodiments in which the secured tube may be removed and resecured firmly in place and including an embodiment in which the tubing may be secured in a vertical or perpendicular position with respect to the body surface or at any angle between 0 and 90° with respect to any body surface.

FIGS. 5A and 5B depict a part of a two-piece catheter tube anchoring system in which a tube tab or tube patch 30 is provided with a covering of release paper as at 32 over a permanent (or releasing reusable) adhesive material 34. The reverse side of the tube tab or tube patch 30 is provided with a releasing readhesible material or other material which functions as one cooperating surface of a two-part readhesible system as at 36 (FIG. 5B). The tube tab 30 is designed to wrap about a catheter tube 38 in a manner such that the adhesive 34 permanently (or optionally removably) secures the tab 30 to the outer surface of the catheter tube 38. The readhesible outer or exposed surface 36 is then used in cooperation with a skin-anchoring patch 40 (FIGS. 6A-6C), as will be explained. The body anchoring or skin patch 40 has a skin anchoring reverse side including a layer of release paper 42 and a skin adhesive material 44 similar to the adhesive layer 15 in the embodiment of FIG. 2. The skin attaching patch 40 further includes a cutout flap segment 46 which is provided with a small segment of release paper 48 which exposes a removably attaching adhesive layer, the back side of which is shown at 50. The removable adhesive layer of the flap segment 46 is designed to wrap about the outer surface 36 of the tube tab 30 as shown in FIG. 6C, thereby firmly attaching the tube 38 to the skin.

The two pieces of the system are normally packed together and, when used, the release paper 32 is removed from the tab 30 and the surface 34 is caused to adhere to the tube 38, at the position desired for the tube to be anchored. Thereafter, the release paper may be removed from the skin attaching patch 40 and the tongue or tab 46 opened away from the skin such that when the adhesive surface 44 of the patch 40 is placed on the skin, the tongue 46 is available to be wrapped about the surface 36 of the tube tab 30, thereby securing the tube tab 30 and the tube 38 in place. When it is desired to remove the cooperating surfaces of the material 50 and the surface 36 can be detached and the tube carrying the tube tab 30 temporarily removed for later replacement. In this manner, the tube 38 is prevented from moving parallel to the long axis of the tube or laterally once fixed in place but may be removed and replaced readily using the system of the invention. The tube tab may also be made removable and replaceable or additional tube tabs provided so that the tube attachment can be changed if desired; or as an alternative to the above embodiment, a system of multiple tube attachment sites to tubes and skin may be provided.

Figure 7B:
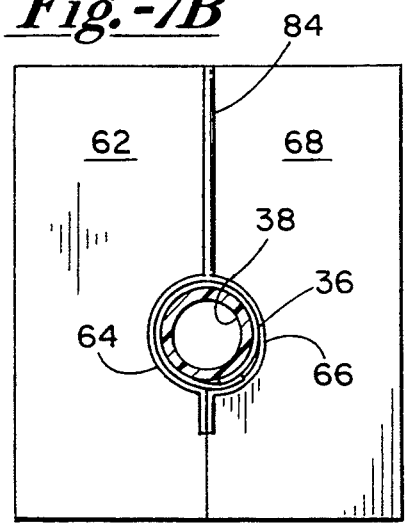
Figure 7C:
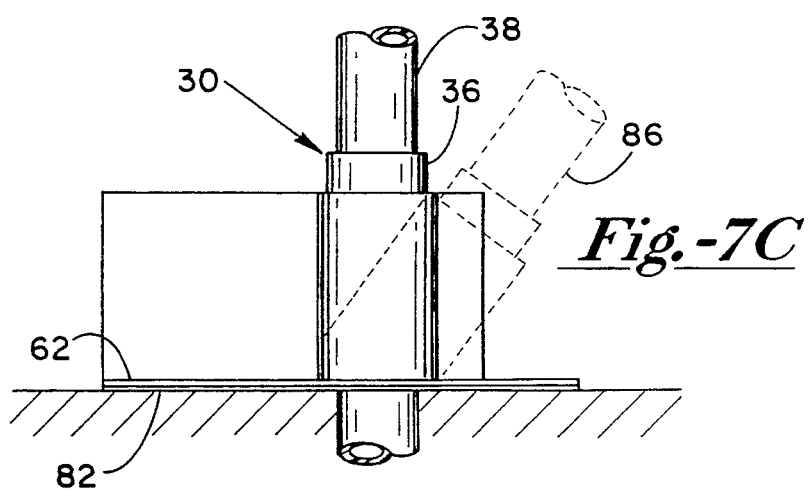

Another embodiment of the invention is depicted in FIGS. 7A-7C which is also designed to operate using a tube tab as at 30 of FIGS. 5A and 5B. In that embodiment, there is provided a skin anchoring portion or skin patch generally at 60 which is divided into segments 62, 64, 66 and 68 separated partially by slits 70, 72 and 74, respectively. The segments 62 and 68 are further provided with oppositely disposed semicircular cutouts 88 and 90 which cooperate to form a circular tube admitting opening when the patch is folded as in FIGS. 7B and 7C. Fold lines are illustrated at 76, 78 and 80 in FIG. 7A. The reverse side of the patch 60 is provided with an adhesive layer as at 82 (FIG. 7C) and suitable release paper (not shown).

The center sections 64 and 66 are designed to fold as shown in FIG. 7B adhering to themselves and forming an outwardly disposed loop 84 extending to the beginning of the slits 70 which separate the lower portion of the segments 64 and 66. The lower portions of the segments 64 and 66 are used to wrap around and encompass the surface 36, with the surplus self-adhering thereby enabling the tube 38 to be held at any desired angle with respect to the skin layer on which the skin adhering patch 60 is placed. Note that in FIG. 7C, the tube 38 is substantially perpendicular to the skin adhering surface, or held at a different angle as shown in phantom at 86. In this manner, the tube 38 can be retained at any desired angle with respect to the anchoring device. Of course, the adhesive material holding the surface 36 to the portions 64 and 66 may be either a permanent adhesive material or a removably repeatably attachable system as discussed above in regard to the embodiment of FIGS. 6A-6C.

In an alternative arrangement, either of slits 70 or 74 (FIG. 7A) may be eliminated and replaced by a continuation of a fold as at 76, 80, respectively, so that one side available to be wrapped around the tube of interest will still be continuously attached to the skin patch to provide greater stability to forces perpendicular to the skin.

As per the above examples, the removable adhesive may be any readhering material that sticks to itself or the surface desired in a releasable readhering manner which achieves a minimum retention force. Of course, the tube tab 30 may itself be provided with a releasable, readherable adhesive material rather than a permanent adhesive so that the tube may be moved using the same readhesible tube tab a plurality of times. The tube adhesive of tab 30 must be one that adheres as desired to the surface of the tube which may be made of any of a number of polymer materials such as silicone and polyethylene. The readhesible adhesive must have the unique characteristic which allows the adhesive surface to stick to itself in such a manner that the adhesive strength will allow one piece of backing material with adhesive to be folded on itself and the adhesive will release when the ends of the backing material are pulled apart and the adhesive will remain firmly attached on the surface of the backing material at all times.

In one experiment, material having an adhesive surface of polyacrylate was caused to come in contact with the outer surface of typical polysiloxane catheter tubing and then stuck to itself for a length about one inch (2.5 cm) beyond the outer diameter of the tubing. Each of the ends of the backing was clamped in a device and force was applied in opposite directions to peel the adhesive back strip apart from itself and the tubing. The amount of force measured required was measured and found to be about 700 g/cm$^2$. This was adequate for retaining the tube as desired and small enough to allow ready removal and readhesion. After 12 sequential adhesive trials of the same strip on the same piece of tubing, the average force required to separate the strip from itself and the tubing was still 500 g/cm$^2$, which was still adequate.

Of course, the materials of the skin patch or skin engaging portion of the anchoring device of the alternate embodiments is preferably one having the same physical properties or attributes as that of the first-described embodiment, including asymmetric stretchability and a modulus which is patterned after that of the skin itself.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different embodiments and that various modifications, both as to equipment details and operating procedures, can be accomplished without departing from the scope of the invention itself.

For example, while the tube anchoring device of the present invention has been described with particular reference to anchoring a urinary catheter tube in several embodiments, it is understood that such a device can be utilized to anchor any type of an ostomy tube including post-surgery drainage tubes placed in various locations in the abdominal or thoracic cavities of the body or to drain other types of wounds during healing. The invention provides a simple yet comprehensive way to support and fix the position of such a tube in a manner which increases patient comfort and the reliability of securing the tube from being pulled out or otherwise displaced from the desired position.

I claim:

1. An anchoring means for securing an elongated tubular member, such as a catheter tube, to be anchored in fixed relation to a substrate comprising:

a tube tab member consisting of a strip of tape material of uniform thickness designed to wrap peripherally about the tube to be secured and carrying a layer of adhesive material on at least one surface thereof, the other surface comprising a first part of a two-part releasable attachment material;

a removable release paper layer initially overlaying the adhesive material on said one surface;

a separate skin-adhering element configured to attach to the skin of a patient and including an integral cutout flap member, the skin-adhering element further carrying a layer of adhesive formulated to attach to the skin on the portion to be attached to the skin and a second part of said two-part releasable attachment material on the cutout flap member;

a further release paper layer initially overlaying the adhesive material on the skin adhering element;

the tube tab member further being configured to wrap around and adhere to the tube at a desired point along the length of the tube using the adhesive on the at least one surface of the tube tab member, the first part of the two-part releasable attachment material on the other surface of the tube tab designed to cooperate with the second part of the two-part releasable attachment material on the cutout flap member of the skin-adhering element when said cutout flap member is wrapped about to peripherally and releasably engage the other surface of the tube tab member thereby releasably fixing the tube in place in relation to the skin-adhering element.

2. The anchoring means of claim 1 wherein the tube tab member, once situated, becomes permanently affixed to the tube.

3. The anchoring means of claim 1 wherein the tube tab member is pre-assembled to the cutout flap member of the skin-adhering element.

4. The anchoring means of claim 1 further comprising a plurality of tube tab members spaced along the length of the tube to be anchored.

5. An anchoring means for securing an elongated catheter tube member in fixed spaced relation to the skin of a patient comprising:

a tube tab element adapted to peripherally adhere to the tube to be secured and carrying a layer of adhesive material on at least one surface thereof, an other surface comprising one part of a two-part releasable attachment material;

a removable release paper layer initially overlaying the adhesive material on the at least one surface;

a skin attaching anchor element adapted to cooperate with the tube tab element, the skin attaching anchor element including a thin sheet of flexible material having a pair of outer zones configured to adhesively attach to the skin of the patient and a pair of inner zone segments therebetween adapted to fold upon themselves and self-adhere, thereby causing the outer sections to come together and forming the pair of inner zone segments into a double-fold central member extending outward from the junction of the two outer segments, the central member and a junction between said outer zones and their adjacent inner zone segments further including slits extending from an outer edge thereof toward the center thereof, each of the outer zones having a semicircular cutout such that when brought together, the pair of semicircular cutouts forms a round cutout for receiving the tube to be anchored, the slit in the central member further being openable to receive and adhesively hold the tube tab element at any disposition between being parallel to the skin and perpendicular thereto.

6. The anchoring means of claim 5 wherein the tube tab element, once situated, becomes permanently affixed to the tube.

7. The anchoring means of claim 5 wherein the tube tab element is designed to be removably fixed both to the tube and to the double folded central member of the skin anchoring element.

8. An anchoring means for securing an elongated tube member in fixed relation to the skin of a patient comprising:

(a) a relatively flat tape strip tube tab element having oppositely disposed inner and outer surfaces and said inner surface adapted to peripherally adhesively adhere to at least a major arc of a peripheral surface of a tube member to be anchored and said tape strip tube tab element carrying a layer of adhesive material on both said inner and outer surfaces thereof, said inner surface adapted to adhere to the tube member carrying an adhesive material selected from the group including releasable adhesive materials and permanent adhesive materials and said outer surface carrying a layer of releasable adhesive; and (b) a separate, skin-adhering, tube-holding anchor element to be used with said tube tab element, the skin-adhering, tube-holding anchor element including, (1) a skin-adhering portion further carrying a layer of adhesive formulated to attach the anchor element to the skin of a patient; and (2) a tube adhering portion configured to wrap around and adhere releasably to said outer surface of said tube tab element, thereby releasably fixing the tube member in place in relation to the skin-adhering, tube-holding anchor element.

* * * * *